(12) United States Patent
Mozdy (10) Patent No.: US 7,349,590 B2
(45) Date of Patent: Mar. 25, 2008

(54) POLARIZATION MODULATION INTERROGATION OF GRATING-COUPLED WAVEGUIDE SENSORS

(75) Inventor: Eric J. Mozdy, Elmira, NY (US)

(73) Assignee: Corning Incorporated, Corning, NY (US)

( * ) Notice: Subject to any disclaimer, the term of this patent is extended or adjusted under 35 U.S.C. 154(b) by 256 days.

(21) Appl. No.: 11/236,060

(22) Filed: Sep. 26, 2005

(65) Prior Publication Data

US 2007/0237447 A1 Oct. 11, 2007

Related U.S. Application Data

(62) Division of application No. 10/627,438, filed on Jul. 25, 2003, now abandoned.

(51) Int. Cl.
*G02B 6/00* (2006.01)
(52) U.S. Cl. .......................................... 385/12; 385/37
(58) Field of Classification Search ................ 385/12, 385/37
See application file for complete search history.

(56) References Cited

U.S. PATENT DOCUMENTS

| | | | |
|---|---|---|---|
| 4,552,578 A | 11/1985 | Anderson | 65/378 |
| 5,008,558 A | 4/1991 | Koshinaka et al. | 250/559.18 |
| 5,094,517 A | 3/1992 | Franke | 385/12 |
| 5,104,222 A | 4/1992 | Kersey et al. | 356/477 |
| 5,479,260 A | 12/1995 | Fattinger | 356/361 |
| 5,738,825 A | 4/1998 | Rudigier et al. | 422/82.11 |
| 5,886,810 A * | 3/1999 | Siahpoushan et al. | 359/285 |
| 6,002,480 A | 12/1999 | Izatt et al. | 356/479 |
| 6,312,961 B1 | 11/2001 | Voirin et al. | 436/518 |
| 6,421,164 B2 | 7/2002 | Tearney et al. | 359/287 |
| 6,455,004 B1 | 9/2002 | Tiefenthaler | 422/91 |
| 6,483,096 B1 | 11/2002 | Kunz et al. | 250/214 R |

(Continued)

OTHER PUBLICATIONS

N.H. Fontaine et al., "Variable-angle internal-reflection Raman spectroscopy for depth-resolved vibrational characterization of polymer thin films", Physical Review B, vol. 57, No. 7, Feb. 15, 1998—1, pp. 3807-3810.

(Continued)

*Primary Examiner*—Ellen E. Kim
(74) *Attorney, Agent, or Firm*—William J. Tucker; Thomas R. Beall (57) ABSTRACT

An optical interrogation system and a GCW sensor are described herein that are used to determine whether a biological substance (e.g., cell, molecule, protein, drug) is located in a sensing region of the GCW sensor. The optical interrogation system includes a light source, a polarization modulator and a detection system. The light source outputs a polarized light beam and the polarization modulator modulates the polarized light beam and outputs a polarization-modulated light beam. The GCW sensor receives and converts the polarization-modulated light beam into an amplitude modulated light beam that is directed towards the detection system. The detection system receives the amplitude modulated light beam and demodulates the received amplitude modulated light beam by responding to signals at a modulation frequency of the polarization-modulated light beam and ignoring noise affecting the signals outside the modulation frequency to detect a resonant condition (e.g., resonant angle, resonant wavelength). The detected resonant condition that has a one-to-one relationship with the refractive index of the superstrate containing the biological substance is analyzed to determine whether or not the biological substance is located in the sensing region of the GCW sensor.

22 Claims, 8 Drawing Sheets

U.S. PATENT DOCUMENTS

| | | | |
|---|---|---|---|
| 6,707,561 B1 * | 3/2004 | Budach et al. | 356/521 |
| 6,903,815 B2 | 6/2005 | Uchiyama et al. | 356/305 |
| 7,186,567 B1 * | 3/2007 | Sutherland et al. | 436/532 |
| 2002/0127565 A1 | 9/2002 | Cunningham et al. | 435/6 |
| 2002/0130262 A1 * | 9/2002 | Nakasuji et al. | 250/311 |
| 2002/0131476 A1 * | 9/2002 | Baba et al. | 374/161 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |
| 2005/0078924 A1 | 4/2005 | Viellerobe et al. | 385/116 |

OTHER PUBLICATIONS

A. Brandenburg et al., "Grating couplers as chemical sensors: a new optical configuration", Sensors and Accuators R, pp. 35-40.

* cited by examiner

POLARIZATION MODULATION INTERROGATION OF GRATING-COUPLED WAVEGUIDE SENSORS

RELATED APPLICATIONS

This application is a Divisional of U.S. patent application Ser. No. 10/627,438, entitled POLARIZATION MODULATION INTERROGATION OF GRATING-COUPLED WAVEGUIDE SENSORS, filed on Jul. 25, 2003, now abandoned in the name of Eric J. Mozdy.

BACKGROUND OF THE INVENTION

1. Field of the Invention

The present invention relates in general to a grating-coupled waveguide (GCW) sensor and, in particular, to an optical interrogation system and method for using polarization-modulated light beams to interrogate a GCW sensor in order to determine whether or not a biological substance is located within a sensing region of the GCW sensor.

2. Description of Related Art

Grating-coupled waveguide (GCW) sensors are fast becoming the technology of choice to enable accurate label-free detection of a biological substance (e.g., cell, drug, chemical compound). This technology typically involves the use of a waveguide evanescent field to sense changes in the refractive index of a GCW sensor caused by the presence of a biological substance in a sensing region of the GCW sensor. To generate the evanescent field, an optical interrogation system is used which has a light source that couples a light beam into a waveguide of the GCW sensor. The optical interrogation system also includes a detector that receives a light beam coupled out from the waveguide that is analyzed to determine the effective refractive index of the waveguide. In determining the effective refractive index of the GCW sensor it should be understood that the light beam received by the detector had interacted with the waveguide under a resonant condition, where the wavevectors of a diffraction grating, incoming light beam, and guided mode all sum to zero. And, that this resonant condition occurs only for a specific wavelength and angle of the incoming light where changes in this angle or wavelength corresponds to changes in the effective refractive index of the waveguide caused by the presence of the biological substance in the sensing region of the GCW sensor. Thus, the optical interrogation system is used to sense a change in the effective index of the GCW sensor which enables one to determine whether or not a biological substance is located within the sensing region of the GCW sensor.

For this technology to be viable, one must have an optical interrogation system and in particular a detector capable of accurately monitoring the resonant angle, wavelength, or both. In particular, the optical interrogation system must emit a light beam that interacts with the GCW sensor, and must in turn receive the light beam coupled-out off the GCW sensor and process that light beam to detect in real time any changes in it's resonant angle and/or wavelength. While there are many approaches for accomplishing these tasks, each has unique implementation challenges, since the light beam output from the GCW sensor is relatively weak and there are multiple sources of noise that degrade this light beam especially in high-throughput screening applications.

GCW sensors are particularly attractive for use in high-throughput screening applications, where the absence of fluorescent tags and the possibility of reduced false-negatives would provide a large cost advantage. For this reason, the microplate has been targeted as the platform for such sensors, where 96 or 384 individual wells provide the high-throughput access demanded by the industry. In this application, the waveguide and diffraction grating of the GCW sensor are located in the bottom of each well; e.g., the diffraction grating may be stamped into the well bottom, and the waveguide subsequently grown on top of the diffraction grating. The wells themselves are typically composed of an optically transparent, low-birefringence, low-cost plastic that is typically several millimeters thick. To probe the GCW sensor in the well bottom while leaving the tops of the wells open for fluid handling, etc., the optical light beam is emitted into the bottom of the microplate and passes through the well plastic before striking the GCW sensor. One source of noise for this type of optical interrogation system is produced by the Fresnel reflection emanating from the bottom surface of each well. Due to the large number of wells, one ideally tries to design the GCW sensor to operate with incoming light beams near normal incidence. As a result, this spurious Fresnel reflection which acts as noise is often inextricably mixed with the light beam output from the GCW sensor that contains the desired information about the resonant angle and/or wavelength. In addition to the Fresnel reflection caused by the bottom surface of the microplate, the top surface of the waveguide inserts yet another Fresnel reflection into the output light beam that mingled with the light beam that propagated as a waveguide mode and exited the GCW sensor through the diffraction grating.

In addition to these direct optical noise sources, the traditional optical interrogation system is susceptible to other electrical and optical noises. For example, the wavelength or angle of the output light beam is often monitored with detectors such as charge-coupled device (CCD) cameras or spectrographs that observe the signal in a DC fashion. All of the DC electrical and optical (stray light) noise can impede the detection of the resonant angle and/or wavelength in the output light beam. Accordingly, there is a need for an optical interrogation system and method that can avoid the aforementioned problematical noise sources when interrogating one or more GCW sensors. This need and other needs are satisfied by the optical interrogation system, GCW sensor and method of the present invention.

BRIEF DESCRIPTION OF THE INVENTION

The present invention includes an optical interrogation system capable of interrogating a GCW sensor to determine whether a biological substance (e.g., cell, molecule, protein, drug) is located in a sensing region of the GCW sensor. The optical interrogation system includes a light source, a polarization modulator and a detection system. The light source outputs a polarized light beam and the polarization modulator modulates the polarized light beam and outputs a polarization-modulated light beam. The GCW sensor receives and converts the polarization-modulated light beam into an amplitude modulated light beam that is directed towards the detection system. The detection system receives the amplitude modulated light beam and demodulates the received amplitude modulated light beam by responding to signals at a modulation frequency of the polarization-modulated light beam and ignoring noise affecting the signals outside the modulation frequency to detect a resonant condition (e.g., resonant angle, resonant wavelength). The detected resonant condition that has a one-to-one relationship with the refractive index of the superstrate containing the biological substance is analyzed to determine whether or not the biological substance is located in the sensing region of the GCW sensor.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
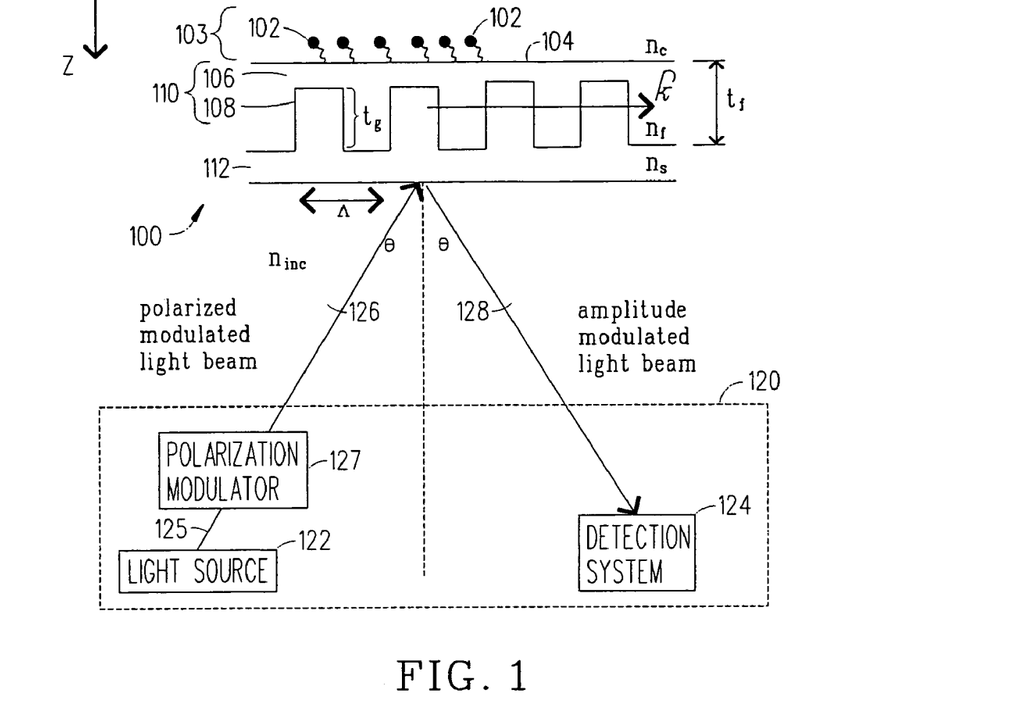
FIG. 1 is a diagram of the basic components of an optical interrogation system and GCW sensor in accordance with the present invention.

Referring to FIG. 1, there is shown a diagram of the basic components of a GCW sensor 100 and an optical interrogation system 120 in accordance with the present invention. Basically, the optical interrogation system 120 interrogates the GCW sensor 100 to determine whether a biological substance 102 (e.g., cell, molecule, protein, drug, chemical compound, nucleic acid, peptide, carbohydrate) is located in a sensing region 103 (superstrate 103) of the GCW sensor 100. The optical interrogation system 120 includes a light source 122, a polarization modulator 127 (e.g., photoelastic modulator 127, photorefractive modulator 127, liquid crystal modulator 127) and a detection system 124. The light source 122 outputs a polarized light beam 125 and the polarization modulator 127 modulates the polarized light beam 125 and outputs a polarization-modulated light beam 126. The GCW sensor 100 receives and converts the polarization-modulated light beam 126 into an amplitude modulated light beam 128 that is directed towards the detection system 124. The detection system 124 receives the amplitude modulated light beam 128 and demodulates the received amplitude modulated light beam 128 by responding to signals at a modulation frequency of the polarization-modulated light beam 126 and ignoring noise affecting the signals outside the modulation frequency to detect a resonant condition (e.g., resonant angle, resonant wavelength). The detected resonant condition has a one-to-one relationship with the refractive index of the superstrate containing the biological substance 102 that indicates whether the biological substance 102 is located in the sensing region 103 of the GCW sensor 100. How the GCW sensor 100 converts the polarization-modulated light beam 126 into the amplitude modulated light beam 128 which enables the optical interrogation system 120 to demodulate the amplitude modulated light beam 128 in a manner that avoids the problems caused by noise sources (e.g., Fresnel reflections, DC electrical and stray light noise) is described in greater detail below after a brief discussion about the basic structure and functionality of the GCW sensor 100.

As shown in FIG. 1, the GCW sensor 100 includes a thin (~100 nm) layer of material 106 (e.g., waveguide film 106) deposited on the surface of a diffraction grating 108 which together form a waveguide 110. The waveguide film 106 is preferably made of a dielectric material such as $Ta_2O_5$, $TiO_2$, $TiO_2$—$SiO_2$, $HfO_2$, $ZrO_2$, $Al_2O_3$, $Si_3N_4$, HfON, SiON, scandium oxides or mixtures thereof. The diffraction grating 108 is formed within a substrate 112 or waveguide film 106 by embossing, holography, or other methods. The diffraction grating 108 can thereby be located above, below, or even within the waveguide film 106. Moreover, the diffraction grating 108 need not be in direct physical contact with a waveguide film 106, simply near enough to cause optical influence on the waveguide mode. Furthermore, due to effective-index waveguiding, the diffraction grating 108 itself can be fabricated with appropriately high enough index to serve as the waveguide itself without the need for an additional waveguide film deposition. The substrate 112 is preferably made of glass or plastic such as cyclic-olefin copolymer (COC). For example, the GCW sensor 100 can have a cyclic-olefin substrate 112 which has an index $n_s$=1.53, a grating pitch Λ=538 mm, a grating thickness is $t_g$=10 mm, a waveguide index $n_f$=2.01, a waveguide thickness $t_f$=110 mm, and a superstrate index that is nominally the index of water (the solvent in which most experiments are performed, $n_c \geq 1.33$). This GCW sensor 100 is referred to herein as the exemplary GCW sensor 100.

The biological substance 102 which may be located within a bulk fluid is introduced to the superstrate 103 (sensing region) of the GCW sensor 100 and it is the presence of this biological substance 102 that alters the index of refraction at the surface 104 of the GCW sensor 100. Thus, to detect the biological substance 102, the GCW sensor 100 is probed with a light beam 126 emitted from the light source 122 and then a reflected light beam 128 received at the detection system 124 is analyzed to determine if there are any changes (~1 part per million) in the refractive index caused by the presence of the biological substance 102 in the sensing region 103 of the GCW sensor 100. In one embodiment, the top surface 104 may be coated with biochemical compounds (not shown) that only allow surface attachment of specific complementary biological substances 102 which enables an GCW sensor 100 to be created that is both highly sensitive and highly specific. In this way, the optical interrogation system 120 and GCW sensors 100 may be used to detect a wide variety of biological substances 102 and if the GCW sensors 100 are arranged in arrays they may be used to enable high throughput drug or chemical screening studies (see FIG. 15).

The sensitivity of the GCW sensor 100 may be best understood by analyzing the structure of the diffraction grating 108 and the waveguide 110. The light beam 126 shone on the diffraction grating 108 can only be coupled into the waveguide 110 if its wave vector satisfies the following resonant condition as shown in equation no. 1:

$$k'_x = k_x - \kappa \quad [1]$$

where $k_x'$ is the x-component of the incident wave vector, $k_x$ is the guided mode wave vector, and κ is the grating vector. The grating vector κ is defined as a vector having a direction perpendicular to the lines of the diffraction grating 108 and a magnitude given by 2π/Λ where Λ is the grating period (pitch). This expression may also be written in terms of wavelength λ and incident angle θ as shown in equation no. 2:

$$\frac{2\pi n_{inc}}{\lambda} \sin\theta = \frac{2\pi n_{eff}}{\lambda} - \frac{2\pi}{\Lambda} \quad [2]$$

Where θ is the angle of incidence of the light beam 126, $n_{inc}$ is the index of refraction of the incident medium, λ is the wavelength of the light 126, and $n_{eff}$ is the effective index of refraction of the waveguide 110. The effective index of the waveguide 110 is a weighted average of the indices of refraction that the optical waveguide mode field or fundamental mode "sees" as it propagates through the waveguide 110. The fundamental mode preferably has a spatial extent that is much wider than the waveguide 110 itself, the extent depending on the refractive index difference between the waveguide 110 and the substrate 112, as well as between the waveguide 110 and the superstrate 103. In particular, the fundamental mode has an evanescent wave/tail that extends into the superstrate 103 (sensing region) which "sees" any surface changes created when the biological substance 102 approaches or comes in contact with the top surface 104 of the GCW sensor 100.

Figure 2:
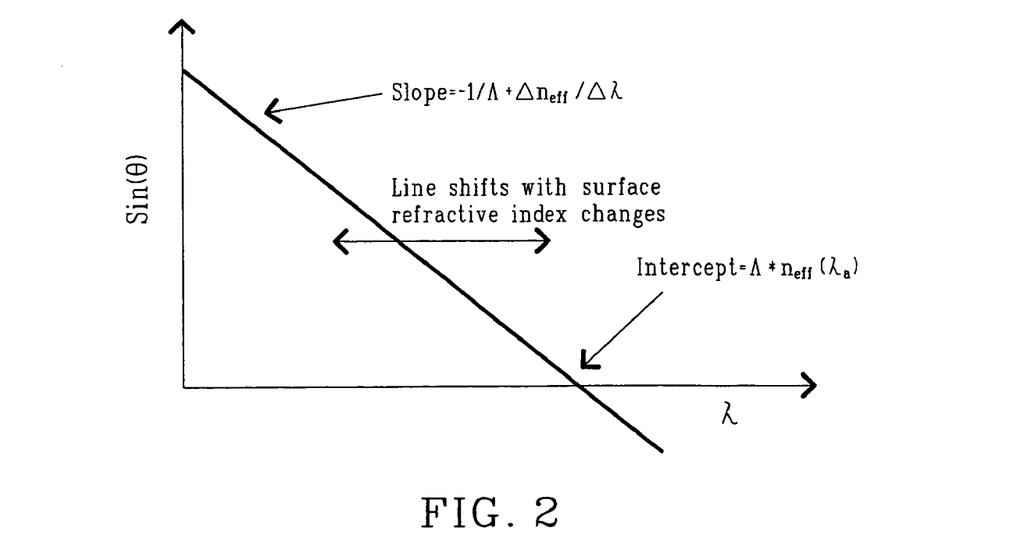
FIG. 2 is a graph that illustrates the relationship between the resonant angle and resonant wavelength of the GCW sensor shown in FIG. 1.

The previous expression shown in equation no. 2 may be rewritten in the more convenient form shown in equation no. 3:

$$\sin\theta = n_{eff} - \frac{\lambda}{\Lambda} \quad [3]$$

which is the equation of a line where sin θ being the y axis, λ being the x-axis, $\Lambda n_{eff}$ the x-intercept, and −1/Λ the slope. To obtain equation no. 3, $n_{inc}$ has been set to 1 so that it could be removed from equation no. 2. This approximation is used since air (n~1.0003) is the most common incident medium. This relation is pictured in the graph shown in FIG. 2. When a biological substance 102 binds to the surface 104, the effective index of the waveguide 110 is altered which leads to the shifting the resonant wavelength or resonant angle of the GCW sensor 100. This shifting can be seen as a shift of the x-intercept in the line shown in FIG. 2.

Figure 3:
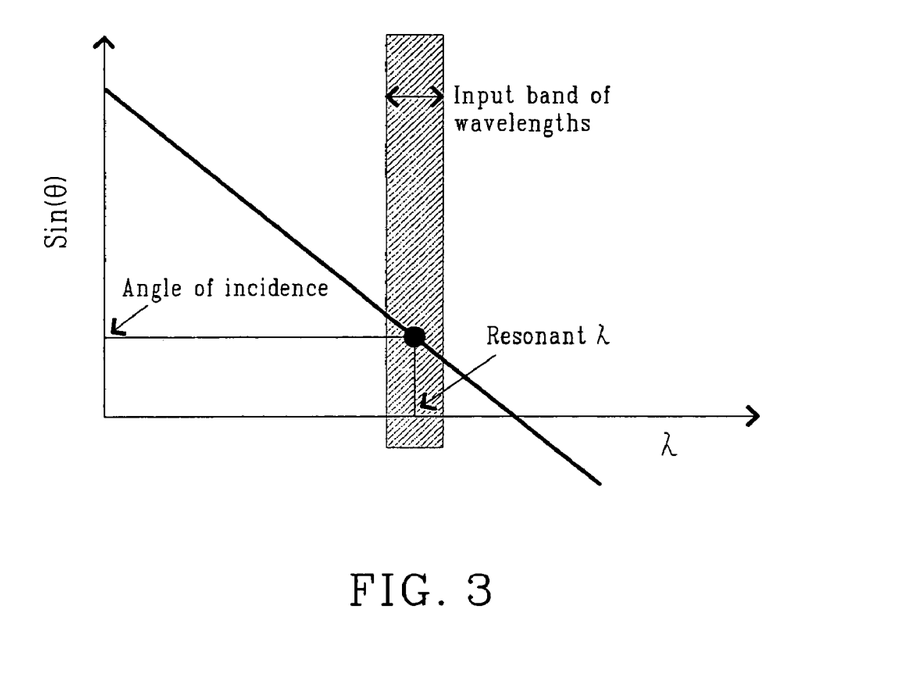
FIG. 3 is a graph used to help describe how a spectral interrogation approach can be used by the optical interrogation system to determine the resonant wavelength of the GCW sensor shown in FIG. 1.
Figure 4:
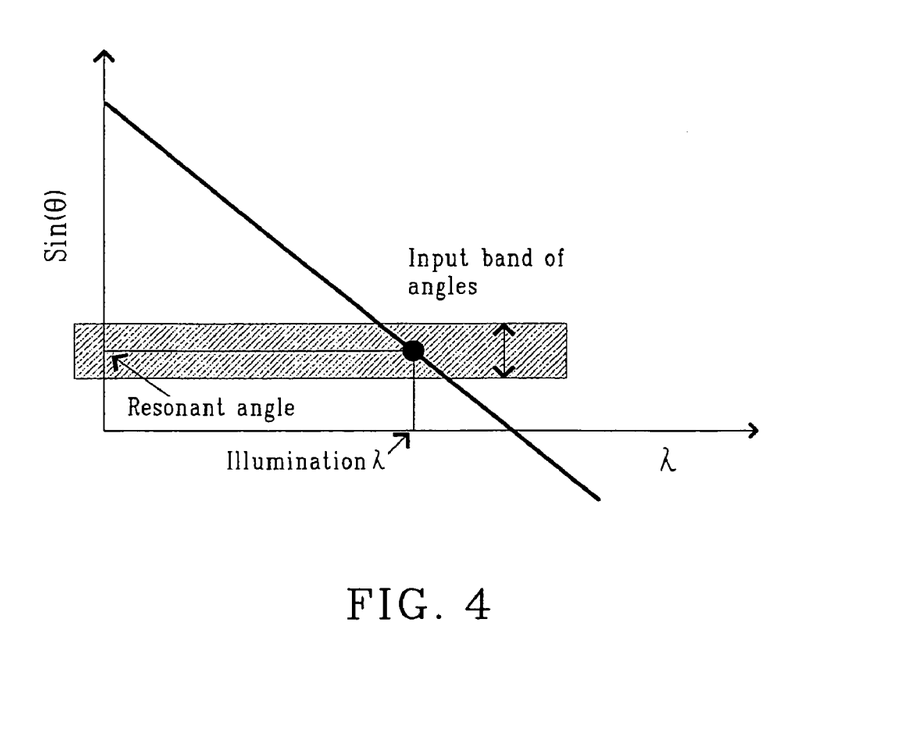
FIG. 4 is a graph used to help describe how an angular interrogation approach can be used by the optical interrogation system to determine the resonant angle of the GCW sensor shown in FIG. 1.

The resonant condition (e.g., resonant wavelength or resonant angle) of such a GCW sensor 100 may be interrogated to determine refractive index changes by observing the reflected light 128 from the GCW sensor 100 (see FIG. 1). There are two different modes of operation for monitoring refractive index changes—spectral interrogation or angular interrogation. In spectral interrogation, a nominally collimated, scanned-wavelength beam of modulated polarized light 126 is sent into the GCW sensor 100 and the reflected amplitude modulated light 128 is collected and monitored by a photodiode (for example) within a detection system 124. By observing the spectral location of the resonant wavelength (peak), one can monitor binding or refractive index changes on or near the surface 104 of the GCW sensor 100. The spectral interrogation concept is graphically represented in the graph shown in FIG. 3. Conversely, in angular interrogation, a nominally single wavelength of modulated polarized light 126 is angle-scanned to create a range of illumination angles and directed into the GCW sensor 100. The reflected amplitude modulated light 128 is monitored by a photodiode (for example) within the detection system 124. By monitoring the position of the resonant angle reflected by the GCW sensor 100, one can monitor binding or refractive index changes on or near the surface 104 of the GCW sensor 100. The angular interrogation concept is graphically represented in the graph shown in FIG. 4.

To maintain simplicity and efficiency of operation, the GCW sensors 100 employed in biosensing applications can be designed such that only the zeroth diffracted orders of the incident light 126 propagate in free space, while what would be the ±1 orders couple to the fundamental mode of the waveguide 110. The higher diffraction orders are avoided by designing a sub-wavelength diffraction grating 108 which has a grating pitch Λ smaller than the desired operating wavelength λ of the incident light 126. In this case, the coupling efficiency of the waveguide 110 is large since multiple orders do not remove power from the GCW sensor 100. Moreover, since only the zeroth reflected and transmitted beams exist in free space, the GCW sensor 100 can thereby produce nearly total reflection or transmission of the desired (anomalous) wavelength λ of the incident light 126.

Figure 5:
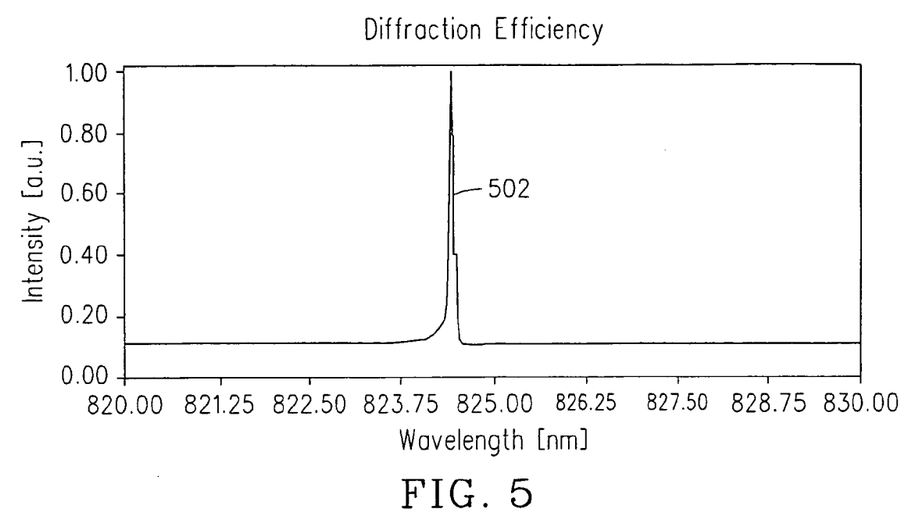
FIG. 5 is a graph generated by GSOLVER that illustrates the resonant wavelength (reflection anomaly) of an exemplary GCW sensor having a substrate made from cyclic-olefin copolymer (COC) and a waveguide film made from $Ta_2O_5$.

FIG. 5 shows a GSOLVER (rigorous coupled-wave analysis, or RCWA code) analysis of an exemplary GCW 100 where the TE input light 126 angle is 3° and the reflected light beam 128 which is at 3° from the normal has a resonance 502 in the vicinity of 824 nm when the substance (water) in the superstrate 103 has an index of 1.33.

Figure 6:
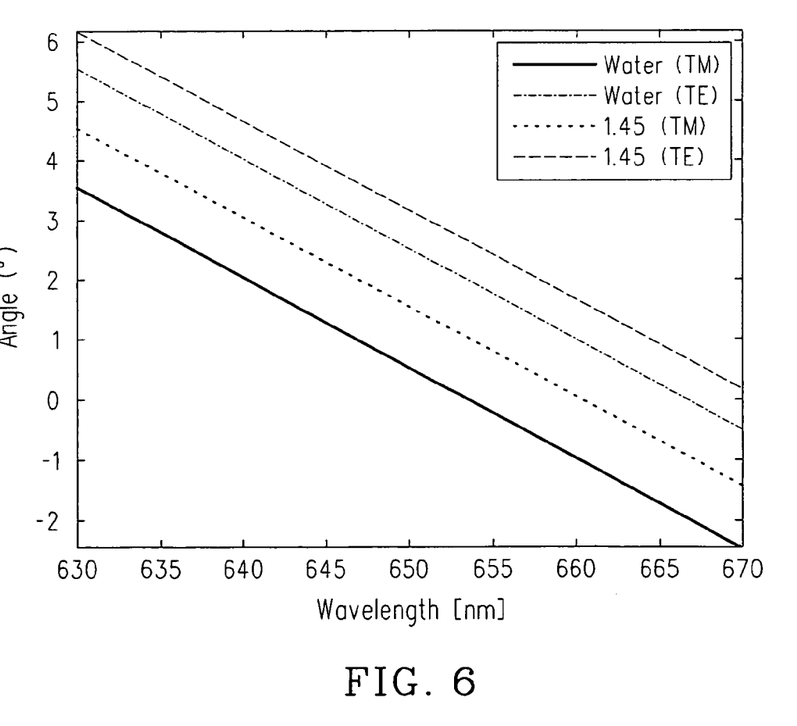
FIG. 6 is a graph illustrating the relationship between the resonant angle and wavelength of an exemplary GCW sensor that has two different cover indices.

As mentioned above, GCW sensors 100 are used in biosensing applications because they enable one to determine the location of the resonance angle/wavelength 502 which directly corresponds to the refractive index of the superstrate 103 and thereby allows the monitoring of biological substance 102 binding on the GCW sensor 100. This is all possible because the evanescent tail of the propagating fundamental mode in the waveguide 110 senses index changes in the superstrate 103 caused by the presence of the biological substance 102. The index change in the supersrate 103 changes the resonance condition of the GCW 100 according equation no. 1 and then the resonance 502 shifts to a new wavelength or angle location. The location of the shifted resonance indicates the current index of the superstrate 103 which indicates whether or not the biological substance 102 is in the superstrate 103 of the GCW 100. It has been shown that the resonance 502 can shift hundreds of nanometers for a unit change in the refractive index of the superstrate 103 (see FIG. 2). The relationship between angle and wavelength is displayed in the graph shown in FIG. 6 for a BIOS-1 GCW sensor 100. The different curves in the graph show behavior for both TE and TM polarizations with two different cover indices.

Referring to FIGS. 7-15, there are illustrated five embodiments of the optical interrogation system 120 shown in FIG. 1 that utilize different approaches to interact with one or more GCW sensors 100 in order to detect the presence of a biological substance 102. Although only five embodiments of the optical interrogation system 120 are described herein, it should be understood that other configurations of the optical interrogation system 120 could be used to interact with the GCW sensor 100 in order to detect the presence of the biological substance 102. Accordingly, the optical interrogation system 120 should not be construed in a limited manner.

Figure 7:
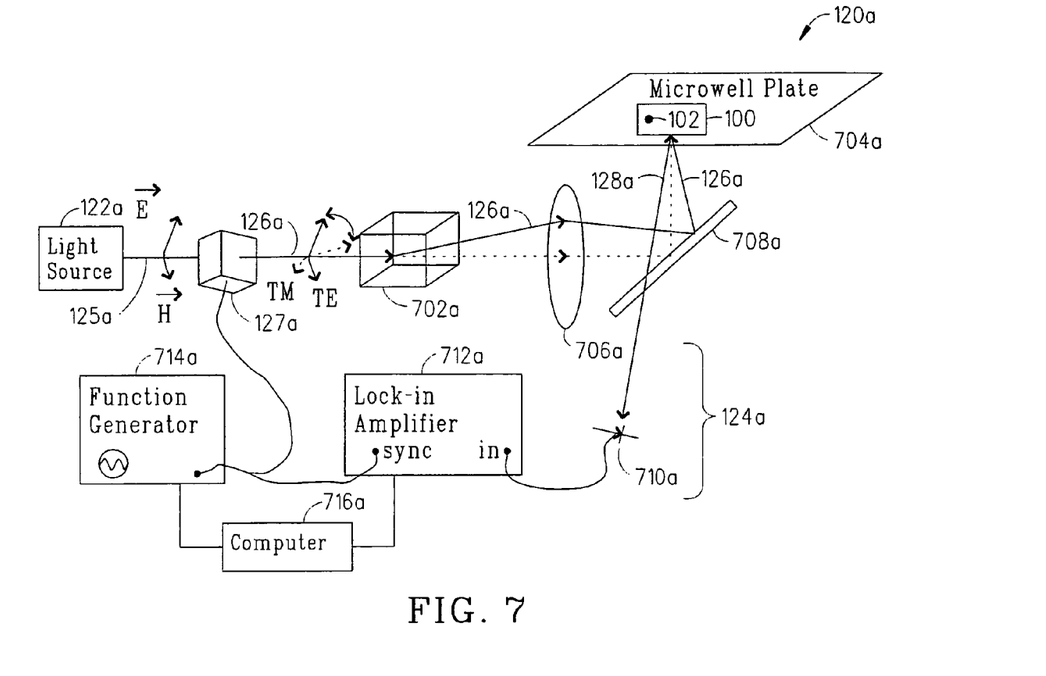
FIG. 7 is a diagram illustrating the basic components of a first embodiment of the optical interrogation system shown in FIG. 1 that utilizes an angular scanning approach to scan a polarization-modulated light beam that is directed into the GCW sensor in order to detect a biological substance in accordance with the present invention.

Referring to FIG. 7, there is a diagram illustrating the basic components of a first embodiment of the optical interrogation system 120a in accordance with the present invention. The optical interrogation system 120a utilizes an angular scanning approach to scan the polarization-modulated light beam 126 that is directed into the GCW sensor 100 in order to enable the detection of the biological substance 102.

As shown, the optical interrogation system 120a includes a light source 122a that outputs a polarized light beam 125a that is received by a polarization modulator 127a (e.g., photoelastic modulator 127a). The polarization modulator 127a modulates the polarized light beam 125a by causing a time-varying polarization alternation between TE and TM modes (see the wobbling vectors in FIG. 7). The polarization modulator 127a outputs the polarization-modulated light beam 126a to an acousto-optic modulator 702a which changes the angle of the polarization-modulated light beam 126a by mixing it with an acoustic wave. The magnitude of the angular deflection depends upon the drive frequency of the acousto-optic modulator 702a and therefore the acoustic wave. In effect, the acousto-optic modulator 702a enables one to control the angular scanning of the polarization-modulated light beam 126a. Since the polarization-modulated light beam 126a should intersect the microwell plate 704a in a constant location, a lens 706a and beamsplitter 708a are placed between the acousto-optic modulator 702a and the microwell plate 704a, where the distance from the lens 706a to each GCW sensor 100 is a focal length. In this manner, the angle of the polarization-modulated light beam 126a incident upon the microwell plate 704a changes with the frequency of the acousto-optic modulator 702a, while the location of the incidence remains constant. After interacting with the GCW sensor 100 in the microwell plate 704a, the polarization-modulated light beam 126a which has only one of the two polarization states resonant within the GCW sensor 100 is converted into the amplitude modulated light beam 128a that is modulated at the same frequency as the polarization-modulated light beam 126a. The amplitude modulated light beam 128a is received by the detection system 124a and in particular by a detector 710a (e.g., photodiode 710a) which converts the amplitude modulated light beam 128a into an electrical signal that is then demodulated by a lock-in amplifier 712a or a similar instrument capable of detecting electrical signals at specific frequencies (e.g., an RF mixer). The lock-in amplifier 712a demodulates the electrical signal by responding to signals at the modulation frequency of the polarization-modulated light beam 126a and ignoring noise affecting the signals outside the modulation frequency. A computer 716a then analyzes the demodulated electrical signal (e.g., a DC voltage proportional to the original modulated reflected optical signal strength) to determine a resonant angle that correlates to the superstrate 103 refractive index and therefore the biological substance content 102 at the sensing region 103 of the GCW sensor 100. The frequency being detected by the lock-in amplifier 712a can be derived from a function generator 714a that also drives the polarization modulator 127a.

The use of the acousto-optic modulator 702a is attractive since it utilizes no moving parts, however other angular scanning techniques can be used in the present invention. For example, a simple rotating plate of glass could be used that deflects the polarization-modulated light beam 126a through refraction at the glass/air interface. The deflection angle depends upon the rotation angle of the glass plate such that the rotating plate causes a smoothly varying angle. The results of several experiments using the optical interrogation system 120a and the exemplary GCW sensor 100 are provided below with respect to FIGS. 8-11.

Figure 8:
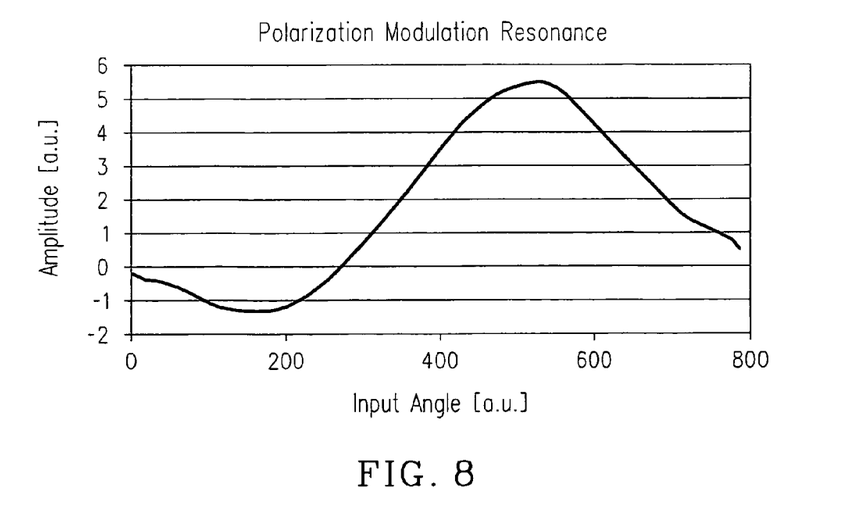
FIG. 8 is a graph that shows the amplitude resonance of an exemplary GCW sensor that was observed when testing the optical interrogation system shown in FIG. 7.

Referring to FIG. 8, there is a graph that shows the resonance observed when testing an experimental optical interrogation system 120a where the amplitude recorded by the lock-in amplifier 712a versus the frequency of the acousto-optic modulator 702a represents the signal. This scan took 0.5 s-2 min. to acquire, and resulted in the very high signal-to-noise curve shown in FIG. 8. It should be noted that the light source 122a (e.g., He/Ne laser 122a) had to be attenuated greatly to avoid saturating the detector 710a (e.g., Si photodiode 710a) and the lock-in amplifier 712a still had many (>5) orders of magnitude of input gain settings to accommodate still lower laser levels.

Figure 9:
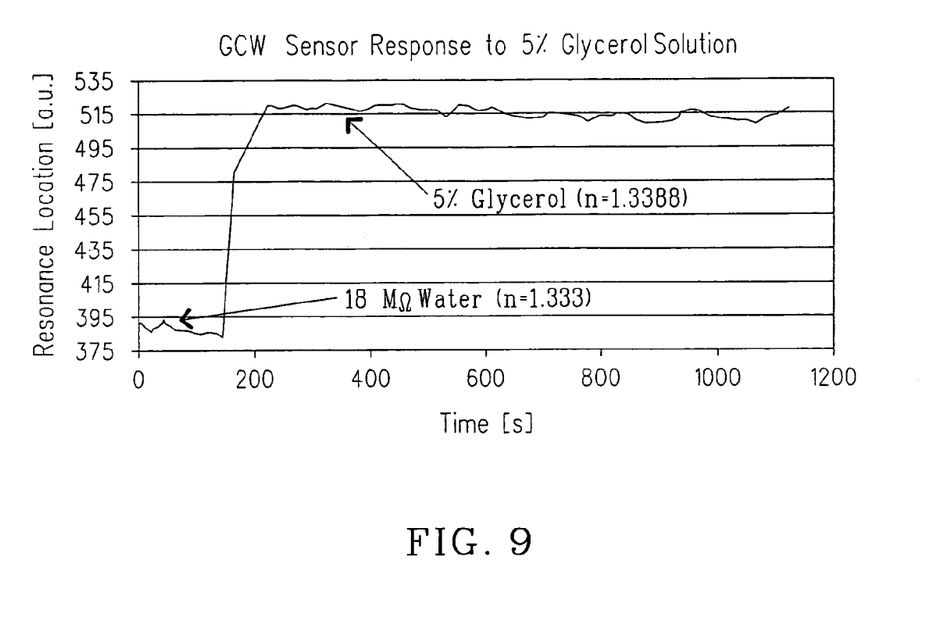
FIG. 9 is a graph that shows the resonance location observed when 5% glycerol solution is placed on top of an exemplary GCW sensor to test the optical interrogation system shown in FIG. 7.

It should be appreciated that the actual sensitivity of the optical interrogation system 120a to biological events depends upon the GCW sensor 100, instrument, angular stability, etc. Thus, to obtain some estimate of the performance of the experimental optical interrogation system 120a, index fluids were placed on the top surface 104 of the GCW sensor 100 to illicit a change in the resonant angle and thereby determine the refractive index unit sensitivity. FIG. 9 shows the result of this study. Noise levels were determined to be as low as $\sim 10^{-5}$ (single standard deviation), and further work indicates that the desired $10^{-6}$ sensitivity is easily achieved with more accurate scanning electronics.

Another important aspect of the present invention, is that the lock-in amplifier 712a provides an extra observable beyond the simple amplitude resonance pictured above in FIG. 8. As a phase-locked technique, the lock-in amplifier 712a provides not only the amplitude of the resonant signal, but also its phase, as referenced to a stable frequency signal such as the electrical function driving the polarization modulator 127a. It should be noted that this information could be obtained with most phase-sensitive detectors (other than a lock-in amplifier 112), or even with a device that can separately monitor the TE and TM polarizations of the amplitude modulated light beam 128a output from the GCW sensor 100.

Figure 10:
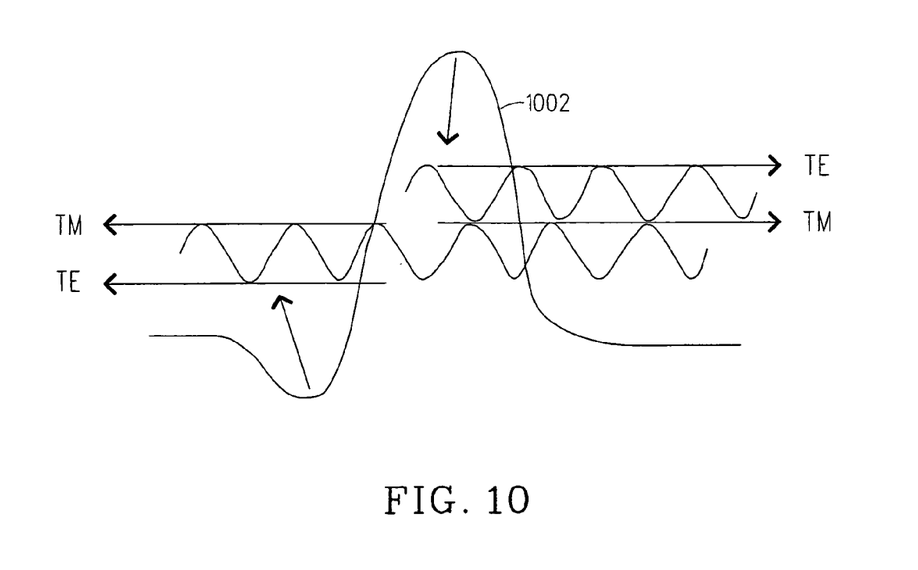
FIG. 10 is a diagram the shows the amplitude resonance of an exemplary GCW sensor that has the characteristic trough/peak shape seen during the testing of the optical interrogation system shown in FIG. 7.

To understand what information the phase signal might present, one can examine the amplitude signal more closely. FIG. 10 shows a diagram of the amplitude resonance 1002 with the characteristic trough/peak shape seen in experiments and theory, where the TE mode has been phase-matched to the GCW sensor 100. The negatively valued dip (source of the arrow on the bottom left of the figure) represents a region where the TE power is below the TM ambient signal, caused by resonantly transmitting the TE light through the GCW sensor 100 (see FIG. 1).) The peak represents the region where the TE light resonantly reflects from the GCW sensor 100, enhancing the power on the detector 710a. Since the TM mode does not interact with the waveguide 110, its level is constant for both the trough and peak. Remembering that the light is modulated between TE and TM modes in time, the curves drawn in FIG. 10 therefore represent the time-varying signal present at the lock-in amplifier 712a at the modulation frequency. By comparing the signals from the peak and trough regions, one can see that the waves are 180° phase-shifted from one another. Moreover, this phase shift should occur at the instant that the amplitude crosses from negative to positive in the center of the resonance.

Figure 11:
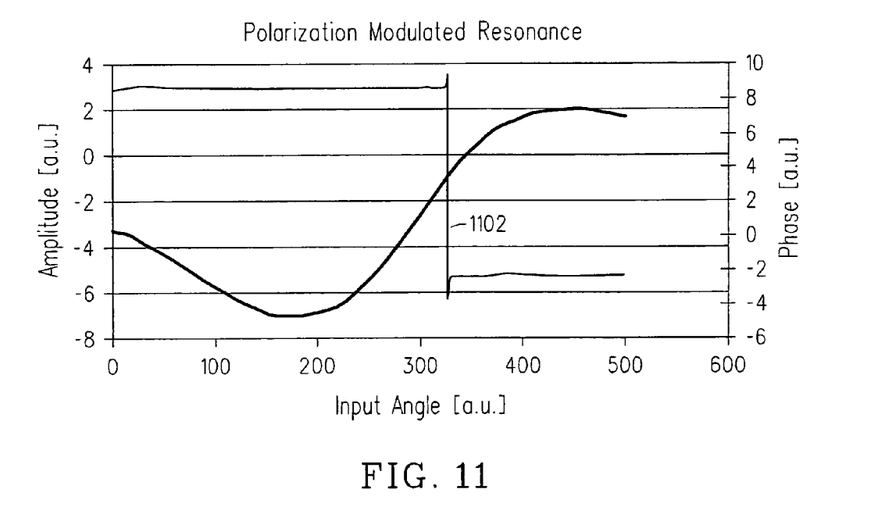
FIG. 11 is a graph that shows the phase of a resonance superimposed on the amplitude plot shown in FIG. 8 when testing the optical interrogation system shown in FIG. 7.

This simple understanding serves to accurately predict what was observed during the experiments with the experimental optical interrogation system 120a. FIG. 11 shows the phase of the resonance 1102 superimposed on the amplitude plot shown in FIG. 8. Since the lock-in amplifier 712a outputs a −10-10 volt signal to the computer 716a to register 360° in phase, the change from ~8 V to ~−2 V represents the 180° phase change indicated in FIG. 11. The transition occurs very close to zero amplitude, where the small difference is actually due to filtering of the amplitude signal that shifts it relative to the phase signal that is acquired at a different time. It should be noticed that this phase transition is extremely steep compared to the resonance amplitude. Moreover, it is akin to a digital indication (on/off) of the resonance location, and therefore represents the simplest signal to detect from a signal processing standpoint. The steepness results from the fact that the transition occurs in a trigger fashion, depending on the relative intensities of the TE/TM modes. Because this signal is so narrow, it could possibly relax the constraints on the resonance width as they relate to detection and location of the resonance. Because the phase signal is inextricably related to the amplitude resonance however, it is not apparent that the localization of the resonance peak will improve using the phase signature, but one may be able to take advantage of signal processing techniques (e.g. a Schmidt trigger) to derive some sensitivity advantage from this phase signal 1102. Assuming this is the case, the width of the amplitude resonance may become less relevant, and allow a whole new class of sensor designs where the width constraints are greatly relaxed.

Figure 12:
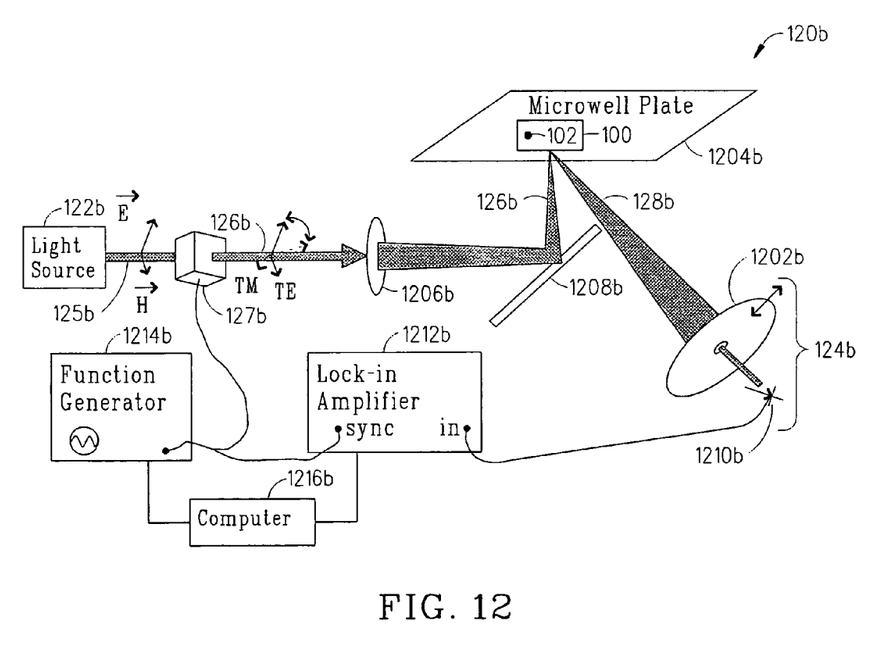
FIG. 12 is a diagram illustrating the basic components of a second embodiment of the optical interrogation system shown in FIG. 1 that utilizes an angular scanning approach to scan an amplitude modulated light beam emitted from the GCW sensor in order to detect a biological substance in accordance with the present invention.

Referring to FIG. 12, there is a diagram illustrating the basic components of a second embodiment of the optical interrogation system 120b. The optical interrogation system 120b utilizes an angular scanning approach to scan the amplitude modulated light beam 128b emitted from the GCW sensor 100 in order to enable the detection of the biological substance 102. As shown, the optical interrogation system 120b includes a light source 122b that outputs a polarized light beam 125b that is received by a polarization modulator 127b (e.g., photoelastic modulator 127b). The polarization modulator 127b modulates the polarized light beam 125b by causing a time-varying polarization alternation between TE and TM modes (see the wobbling vectors in FIG. 12). The polarization modulator 127b outputs the polarization-modulated light beam 126b to a lens 1206b and beamsplitter 1208b. The lens 1206b and beamsplitter 1208b direct the polarization-modulated light beam 126b to the GCW sensor 100 within the microwell plate 1204b. After interacting with the GCW sensor 100 in the microwell plate 1204b, the polarization-modulated light beam 126b which has only one of the two polarization states resonant within the GCW sensor 100 is converted into the amplitude modulated light beam 128b that is modulated at the same frequency as the polarization-modulated light beam 126b. The amplitude modulated light beam 128b is received by the detection system 124b and in particular by a scanning pinhole plate 1202b that scans the angle of the amplitude modulated light beam 128b. The detector 1210b (e.g., photodiode 1210b) converts the scanned amplitude modulated light beam 128b into an electrical signal that is then demodulated by a lock-in amplifier 1212b. The lock-in amplifier 1212b demodulates the electrical signal by responding to signals at the modulation frequency of the polarization-modulated light beam 126b and ignoring noise affecting the signals outside the modulation frequency. A computer 1216b then analyzes the demodulated electrical signal (e.g., a DC voltage proportional to the original modulated reflected optical signal strength) to determine a resonant angle that correlates to the superstrate 103 refractive index and therefore the biological substance content 102 at the sensing region 103 of the GCW sensor 100. The frequency being detected by the lock-in amplifier 1212b can be derived from a function generator 1214b that also drives the polarization modulator 127b.

Figure 13:
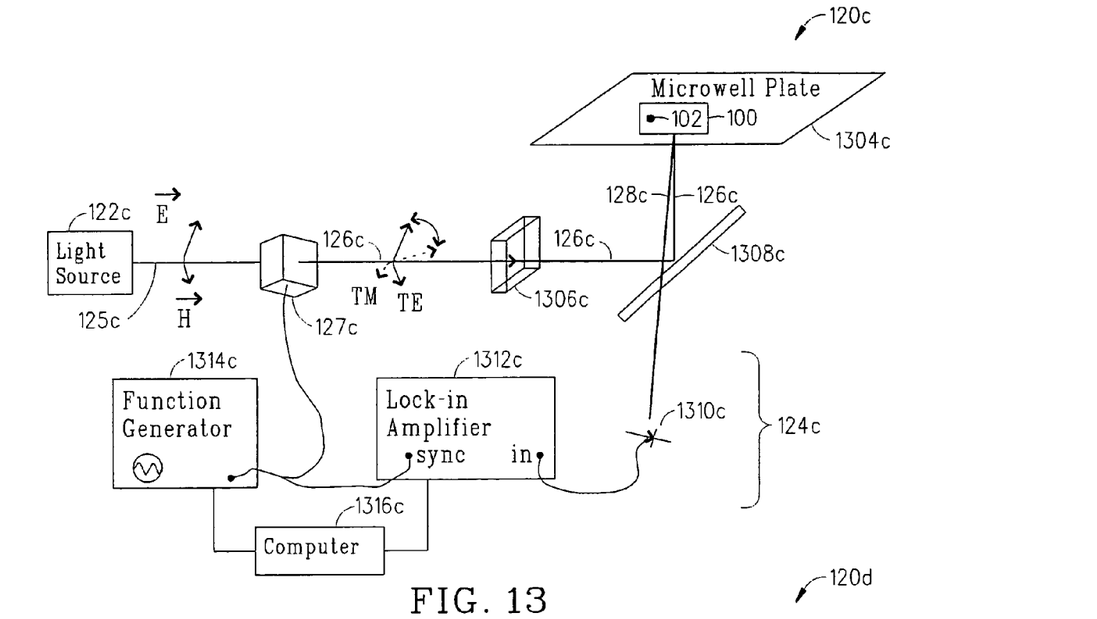
FIG. 13 is a diagram illustrating the basic components of a third embodiment of the optical interrogation system shown in FIG. 1 that utilizes a wavelength scanning approach to scan a polarization-modulated light beam that is directed into the GCW sensor in order to detect a biological substance in accordance with the present invention.

Referring to FIG. 13, there is a diagram illustrating the basic components of a third embodiment of the optical interrogation system 120c. The optical interrogation system 120c utilizes a wavelength scanning approach to scan the polarization-modulated light beam 126c directed into the GCW sensor 100 in order to enable the detection of the biological substance 102. As shown, the optical interrogation system 120c includes a broadband light source 122c that outputs a polarized light beam 125c that is received by a polarization modulator 127c (e.g., photoelastic modulator 127c). The polarization modulator 127c modulates the polarized light beam 125c by causing a time-varying polarization alternation between TE and TM modes (see the wobbling vectors in FIG. 13). The polarization modulator 127c outputs the polarization-modulated light beam 126c to a tunable filter 1306c. The tunable filter 1306c scans the wavelength of the polarization-modulated light beam 126c and directs the scanned polarization-modulated light beam 126c to a beamsplitter 1308c. The beamsplitter 1308c directs the polarization-modulated light beam 126c to the GCW sensor 100 within the microwell plate 1304c. After interacting with the GCW sensor 100 in the microwell plate 1304c, the polarization-modulated light beam 126c which has only one of the two polarization states resonant within the GCW sensor 100 is converted into the amplitude modulated light beam 128c that is modulated at the same frequency as the polarization-modulated light beam 126c. The amplitude modulated light beam 128c is received by the detection system 124b and in particular by a detector 1310c (e.g., photodiode 1310c) which converts the amplitude modulated light beam 128c into an electrical signal that is then demodulated by a lock-in amplifier 1312c. The lock-in amplifier 1212c demodulates the electrical signal by responding to signals at the modulation frequency of the polarization-modulated light beam 126c and ignoring noise affecting the signals outside the modulation frequency. A computer 1316c then analyzes the demodulated electrical signal (e.g., a DC voltage proportional to the original modulated reflected optical signal strength) to determine a resonant angle that correlates to the superstrate 103 refractive index and therefore the biological substance content 102 at the sensing region 103 of the GCW sensor 100. The frequency being detected by the lock-in amplifier 1312c can be derived from a function generator 1314c that also drives the polarization modulator 127c.

Figure 14:
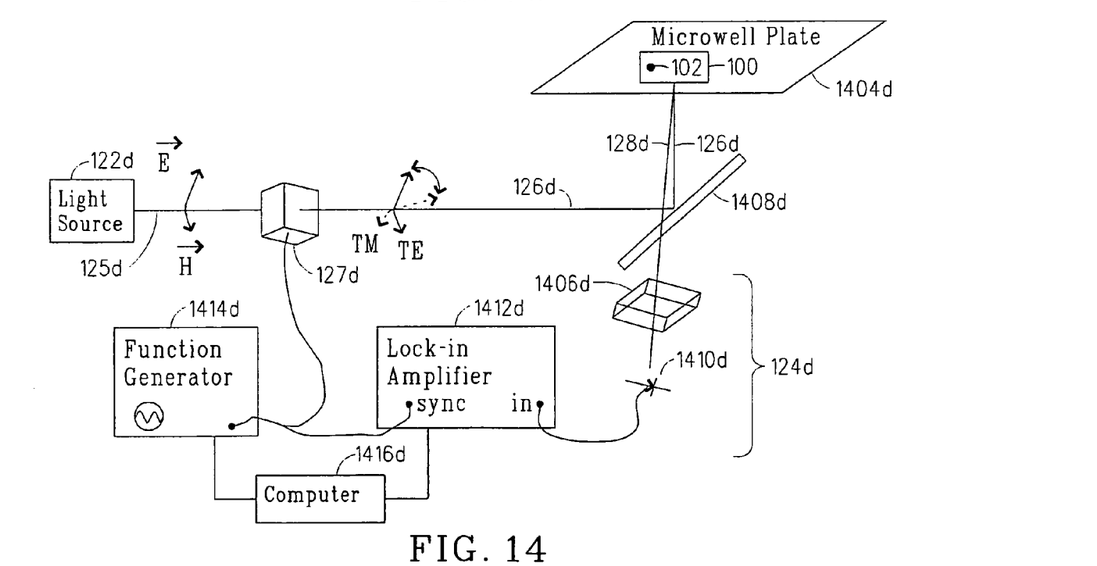
FIG. 14 is a diagram illustrating the basic components of a fourth embodiment of the optical interrogation system shown in FIG. 1 that utilizes a wavelength scanning approach to scan an amplitude modulated light beam emitted from the GCW sensor in order to detect a biological substance in accordance with the present invention.

Referring to FIG. 14, there is a diagram illustrating the basic components of a fourth embodiment of the optical interrogation system 120d. The optical interrogation system 120d utilizes an wavelength scanning approach to scan the amplitude modulated light beam 128d emitted from the GCW sensor 100 in order to enable the detection of the biological substance 102. As shown, the optical interrogation system 120d includes a broadband light source 122d that outputs a polarized light beam 125d that is received by a polarization modulator 127d (e.g., photoelastic modulator 127d). The polarization modulator 127d modulates the polarized light beam 125d by causing a time-varying polarization alternation between TE and TM modes (see the wobbling vectors in FIG. 14). The polarization modulator 127d outputs the polarization-modulated light beam 126d to a beamsplitter 1408d. The beamsplitter 1408d directs the polarization-modulated light beam 126d to the GCW sensor 100 within the microwell plate 1404d. After interacting with the GCW sensor 100 in the microwell plate 1404d, the polarization-modulated light beam 126d which has only one of the two polarization states resonant within the GCW sensor 100 is converted into the amplitude modulated light beam 128d that is modulated at the same frequency as the polarization-modulated light beam 126d. The amplitude modulated light beam 128d is received by the detection system 124d and in particular by a scanning filter 1406d that scans the wavelength of the amplitude modulated light beam 128d. The detector 1410d (e.g., photodiode 1210d) converts the scanned amplitude modulated light beam 128d into an electrical signal that is then demodulated by a lock-in amplifier 1412d. The lock-in amplifier 1412d demodulates the electrical signal by responding to signals at the modulation frequency of the polarization-modulated light beam 126d and ignoring noise affecting the signals outside the modulation frequency. A computer 1416d then analyzes the demodulated electrical signal (e.g., a DC voltage proportional to the original modulated reflected optical signal strength) to determine a resonant angle that correlates to the superstrate 103 refractive index and therefore the biological substance content 102 at the sensing region 103 of the GCW sensor 100. The frequency being detected by the lock-in amplifier 1412d can be derived from a function generator 1414d that also drives the polarization modulator 127d.

Figure 15:
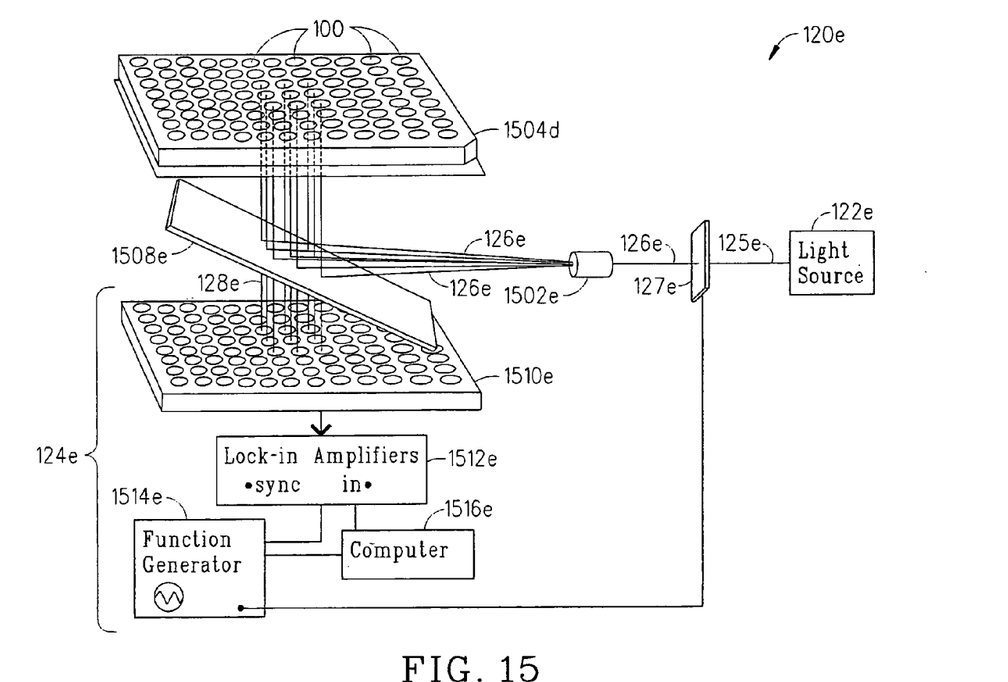
FIG. 15 is a diagram illustrating the basic components of a fifth embodiment of the optical interrogation system shown in FIG. 1 that can utilize an angular or wavelength scanning approach to scan an array of GCW sensors incorporated within a microplate in accordance with the present invention.

Referring to FIG. 15, there is a diagram illustrating the basic components of a fifth embodiment of the optical interrogation system 120e. The optical interrogation system 120e utilizes a parallel angle/wavelength scanning approach to scan multiple polarization-modulated light beams 126e directed to multiple GCW sensors 100 to enable the high-throughput detection of biological substances 102. As shown, the optical interrogation system 120e includes a light source 122e that outputs a polarized light beam 125e that is received by a polarization modulator 127e (e.g., photoelastic modulator 127e). The polarization modulator 127e modulates the polarized light beam 125e by causing a time-varying polarization alternation between TE and TM modes and outputs the polarization-modulated light beam 126e to a diffractive optic 1502e. The diffractive optic 1502e emits an array of polarization-modulated light beams 126e to a beamsplitter 1508e. The beamsplitter 1508e directs the polarization-modulated light beams 126e to the GCW sensors 110 within the microwell plate 1504d. After interacting with the GCW sensors 100 in the microwell plate 1504e, the polarization-modulated light beams 126d are converted into the amplitude modulated light beams 128e that are modulated at the same frequency as the polarization-modulated light beams 126e. The amplitude modulated light beams 128e are received by the detection system 124e and in particular by an array of detectors 1510e (e.g., photodiodes 1510e) which converts the scanned amplitude modulated light beams 128e into electrical signals that are then demodulated by an array of lock-in amplifiers 1512e. The lock-in amplifiers 1512e demodulate the electrical signals by responding to signals at the modulation frequency of the polarization-modulated light beam 126e and ignoring noise affecting the signals outside the modulation frequency. A computer 1516e then analyzes the demodulated electrical signal (e.g., a DC voltage proportional to the original modulated reflected optical signal strength) to determine a resonant angle that correlates to the superstrate 103 refractive index and therefore the biological substance content 102 at the sensing region 103 of the GCW sensor 100. The frequency being detected by the lock-in amplifiers 1512e can be derived from a function generator 1514e that also drives the polarization modulator 127e. It should be appreciated that the configuration of this optical interrogation system 120e is only one of many different possible configurations that can be used in high-throughput screening applications. Basically, this invention can be applied to all multiplexed, scanning, etc. systems that are compatible with polarization modulation.

Although FIG. 15 does not explicitly show the components required to scan the angle or wavelength as per one of the many embodiments shown in FIGS. 7, 12, 13, or 14. It is assumed that one of these scanning techniques (or a suitable substitute) would be employed together with the components of FIG. 15 to achieve a system that scans the GCW 100 resonance over every well. For the embodiments of FIGS. 7 and 13, only one scanning element (acousto-optic modulator or filter) need be placed before the diffractive optic, thereby copying the scanning behavior to each separate beam. In the embodiments of FIGS. 12 and 14, the scanning apparatus (pinhole or filter) would likely be required in duplicate for each beam reflected from each well of the plate.

Figure 16:
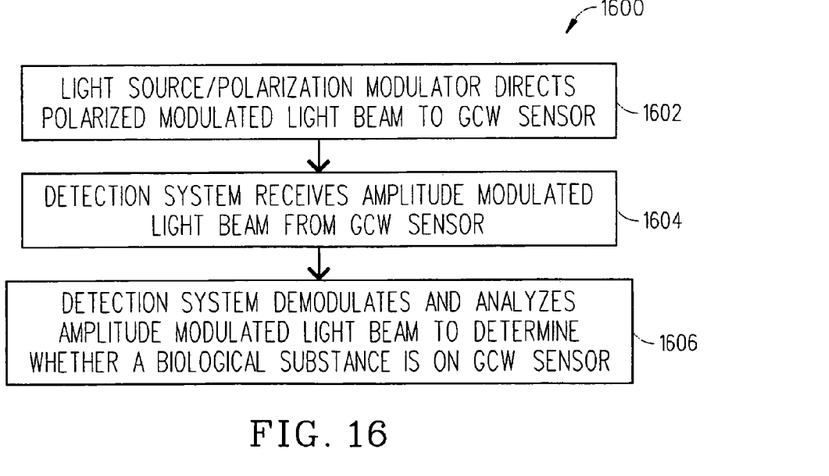
FIG. 16 is a flowchart illustrating the basic steps of a preferred method for using the optical interrogation system and GCW sensor shown in FIG. 1 to detect a biological substance in accordance with the present invention.

Referring to FIG. 16, there is a flowchart illustrating the basic steps of a preferred method for using the optical interrogation system 120 and GCW sensor 100 to detect a biological substance 102 in accordance with the present invention. Although the GCW sensor 100 and optical interrogation system 120 are described herein as being used to detect the presence of biological substances 102 like cells, molecules, proteins, drugs, chemical compounds, nucleic acids, peptides or carbohydrates on the surfaces 104 of the GWC sensor 100, it should be understood that the GCW sensor 100 and optical interrogation system 120 can be used to perform a wide variety of studies. For example, the GCW sensor 100 and optical interrogation system 120 can be used to perform cell migration assays, drug permeability assays, drug solubility studies, virus detection studies and protein secretion studies.

Beginning at step 1602, the light source 122 and polarization modulator 127 are used to direct a polarization-modulated light beam 126 to the GCW sensor 100. At step 1604, the detection system 124 receives an amplitude modulated light beam 128 from the GCW sensor 100. Then at step 1606, the detection system 124 demodulates and analyzes the received amplitude modulated light beam 128 to detect a resonant wavelength or resonant angle which corresponds to a superstrate 103 refractive index that indicates whether a biological substance 102 is located on the surface 104 of the GCW sensor 100.

Following are some advantages and uses of the optical interrogation system 120 and GCW sensors 100 of the present invention:

The use of polarization modulation in accordance with the present invention enables one to use large-area photodiodes that provides a cost advantage and robustness to the instrument design not currently available with traditional optical interrogation systems. Moreover, the use of large area detectors greatly relaxes the performance (flatness, etc.) required from the sensor wellplate. Basically, the reflected beam simply has to hit the photodiode somewhere in its area to be correctly detected and decoded. The only constraint in this situation is that the beams from separate wells do not "cross" each other in the farfield. In other words, each beam should retain its relationship relative to its neighbors, although neighbor proximity may vary from well to well. This is a much less stringent condition than would be required for coupling back into optical fiber, for example, or imaging the reflections onto CCDs used by traditional optical interrogation systems.

The use of polarization modulation in accordance with the present invention can be applied to nearly every instrument designed to interrogate grating-coupled biosensors. The invention involves the overlay of polarization modulation and coherent (phase-sensitive) detection onto the structures of the traditional optical interrogation systems. This is true regardless of whether angle, wavelength or some other parameter is being scanned, either on the input or output of the GCW sensor 100.

The present invention removes a large number of noise sources by taking advantage of optical beam polarization.

The present invention drastically reduces the required power for detection of biological substances. As a result, the milliwatts of power typically required of the output beam for sensitive detection by a CCD element is reduced several orders of magnitude under this invention. This is very important for the high-throughput screening market, since 96, 384, or even 1536 wells may be interrogated in parallel with the same optical (laser) source.

In addition to the signal-to-noise improvements associated with the present invention, there are several other equally important benefits of the technology. First, because the polarization modulation technique obtains high signal-to-noise data from ordinary photodiodes, the cost and complexity of the instrumentation can be greatly reduced compared to the expensive CCD or spectrograph solutions used by traditional optical interrogation systems. Moreover, the scale-up of the optical interrogation system 120 to accommodate 96 or 384 wells in a plate becomes much easier since one only needs to use more inexpensive detectors and lock-in amplifiers.

In addition to the cost and complexity advantage of the present invention, the use of lock-in amplifiers provides phase information about the resonance previously unavailable. The presence of both amplitude and phase information from the phase-sensitive detection provides an extra observable. As discussed above, this phase information actually contains a convenient and unique signal that indicates the resonance location.

The polarization modulation concept of the present invention can be implemented within most interrogation schemes (e.g., angular or wavelength-based approaches). It simply requires that the polarization be modulated in order to distinguish the waveguide output from noise, somewhat independent of the other variables of the system. In one embodiment of this invention, one could modulate the input beam polarization much faster than the angular scanning rate, such that the angular position is essentially constant during the demodulation process for each angular step.

As described above, the preferred modulation method is photoelastic, where a quartz plate is vibrated to produce time-variable birefringence due to the photoelastic effect. This technology is preferred both for the purity of polarization modulation as well as high available modulation frequency, 100 kHz.

Although the preferred embodiments of the present invention described above utilized a reflected light beam to enable the detection of the biological substance, it should be readily appreciated that a transmitted beam and even a beam exiting the side of the sensor could also be used to detect the biological substance. Of course, minor changes to the set-up of the system would be required to detect the transmitted beam or the beam exiting the side of the sensor.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An optical interrogation system for interrogating a grating-coupled waveguide sensor, said optical interrogation system comprising:

a light source capable of outputting a polarized light beam;

a polarization modulator capable of modulating the polarized light beam and outputting a polarization-modulated light beam;

said grating-coupled waveguide sensor capable of receiving the polarization-modulated light beam and converting the polarization-modulated light beam into an amplitude modulated light beam;

a light beam scanning device capable of angular scanning or wavelength scanning the polarization-modulated light beam prior to being directed towards said grating-coupled waveguide sensor or capable of angular scanning or wavelength scanning the amplitude modulated light beam received from said grating-coupled waveguide sensor;

a detector capable of receiving the amplitude modulated light beam and further capable of converting the amplitude modulated light beam into an electrical signal;

a lock-in amplifier capable of receiving the electrical signal from said detector and further capable of demodulating the electrical signal a computer capable of analyzing the demodulated electrical signal to detect a resonant condition which indicates whether a biological substance is located in a sensing region of said grating-based waveguide sensor; and a function generator capable of synchronizing said polarization modulator and said lock-in amplifier.

2. The optical interrogation system of claim 1, wherein said biological substance is a cell, molecule, protein, drug, chemical compound, nucleic acid, peptide or carbohydrate.

3. The optical interrogation system of claim 1, wherein said polarization modulator is a photoelastic modulator.

4. The optical interrogation system of claim 1, wherein said polarization modulator is a photorefractive modulator.

5. The optical interrogation system of claim 1, wherein said polarization modulator is a liquid crystal modulator.

6. The optical interrogation system of claim 1, wherein said grating-coupled waveguide sensor is located within a microplate.

7. The optical interrogation system of claim 1, wherein said light beam scanning device is an acousto-optic modulator, a scanning pinhole plate, a tunable filter or a scanning filter.

8. The optical interrogation system of claim 7, wherein said computer uses phase information within said demodulated electrical signal to identify the resonant condition which indicates whether the biological substance is located in the sensing region of said grating-coupled waveguide sensor.

9. The optical interrogation system of claim 7, wherein said computer uses amplitude information within said demodulated electrical signal to identify the resonant condition which indicates whether the biological substance is located in the sensing region of said grating-coupled waveguide sensor.

10. An optical interrogation system for interrogating a grating-coupled waveguide sensor, said optical interrogation system comprising:

a light source capable of outputting a polarized light beam;

a polarization modulator capable of modulating the polarized light beam and outputting a polarization-modulated light beam;

an angular scanning device capable of receiving the polarization-modulated light beam from said polarization modulator and further capable of scanning the angle of the polarization-modulated light beam;

a lens capable of receiving the polarization-modulated light beam from said angular scanning device;

a beam splitter capable of receiving the polarization-modulated light beam from said lens;

said grating-coupled waveguide sensor capable of receiving the polarization-modulated light beam from said beam splitter and converting the polarization-modulated light beam into an amplitude modulated light beam;

a detector capable of receiving the amplitude modulated light beam from said grating-coupled waveguide sensor and further capable of convening the amplitude modulated light beam into an electrical signal;

a lock-in amplifier capable of receiving the electrical signal from said detector and further capable of demodulating the electrical signal;

a computer capable of analyzing the demodulated electrical signal to detect a resonant condition which indicates whether a biological substance is located in a sensing region of said grating-based waveguide sensor; and a function generator capable of synchronizing said polarization modulator and said lock-in amplifier.

11. An optical interrogation system for interrogating a grating-coupled waveguide sensor, said optical interrogation system comprising:

a light source capable of outputting a polarized light beam;

a polarization modulator capable of modulating the polarized light beam and outputting a polarization-modulated light beam;

a lens capable of receiving the polarization-modulated light beam from said polarization modulator;

a beam splitter capable of receiving the polarization-modulated light beam from said lens;

said grating-coupled waveguide sensor capable of receiving the polarization-modulated light beam from said beam splitter and converting the polarization-modulated light beam into an amplitude modulated light beam;

a scanning pinhole plate capable of receiving the amplitude modulated light beam from said grating-coupled waveguide sensor and further capable of scanning the angle of amplitude modulated light beam;

a detector capable of receiving the amplitude modulated light beam from said scanning pinhole plate and further capable of converting the amplitude modulated light beam into an electrical signal;

a lock-in amplifier capable of receiving the electrical signal from said detector and further capable of demodulating the electrical signal;

a computer capable of analyzing the demodulated electrical signal to detect a resonant condition which indicates whether a biological substance is located in a sensing region of said grating-based waveguide sensor; and a function generator capable of synchronizing said polarization modulator and said lock-in amplifier.

12. An optical interrogation system for interrogating a grating-coupled waveguide sensor, said optical interrogation system comprising:

a light source capable of outputting a polarized light beam;

a polarization modulator capable of modulating the polarized light beam and outputting a polarization-modulated light beam;

a tunable filter capable of receiving the polarization-modulated light beam from said polarization modulator and further capable of scanning the wavelength of the polarization-modulated light beam;

a beam splitter capable of receiving the polarization-modulated light beam from said tunable filter;

said grating-coupled waveguide sensor capable of receiving the polarization-modulated light beam from said beam splitter and convening the polarization-modulated light beam into an amplitude modulated light beam;

a detector capable of receiving the amplitude modulated light beam from said grating-coupled waveguide sensor and further capable of converting the amplitude modulated light beam into an electrical signal;

a lock-in amplifier capable of receiving the electrical signal from said detector and further capable of demodulating the electrical signal;

a computer capable of analyzing the demodulated electrical signal to detect a resonant condition which indicates whether a biological substance is located in a sensing region of said grating-based waveguide sensor; and a function generator capable of synchronizing said polarization modulator and said lock-in amplifier.

13. An optical interrogation system for interrogating a grating-coupled waveguide sensor, said optical interrogation system comprising:

a light source capable of outputting a polarized light beam;

a polarization modulator capable of modulating the polarized light beam and outputting a polarization-modulated light beam;

a beam splitter capable of receiving the polarization-modulated light beam from said polarization modulator;

said grating-coupled waveguide sensor capable of receiving the polarization-modulated light beam from said beam splitter and convening the polarization-modulated light beam into an amplitude modulated light beam;

a scanning filter capable of receiving the amplitude modulated light beam from said grating-coupled waveguide sensor and further capable of scanning the wavelength of the amplitude modulated light beam;

a detector capable of receiving the amplitude modulated light beam from said scanning filter and further capable of converting the amplitude modulated light beam into an electrical signal;

a lock-in amplifier capable of receiving the electrical signal from said detector and further capable of demodulating the electrical signal;

a computer capable of analyzing the demodulated electrical signal to detect a resonant condition which indicates whether a biological substance is located in a sensing region of said grating-based waveguide sensor; and a function generator capable of synchronizing said polarization modulator and said lock-in amplifier.

14. A method for interrogating one or more grating-coupled waveguide sensors, said method comprising the steps of:

directing a polarization-modulated light beam into each grating-coupled waveguide sensor;

receiving an amplitude modulated light beam from each grating-coupled waveguide sensor; and processing each received amplitude modulated light beam to detect a resonant condition which corresponds to a superstrate refractive index that indicates whether a biological substance is located in a sensing region of the respective grating-coupled waveguide sensor, wherein said processing step further includes:

converting each received amplitude modulated light beam into an electrical signal;

demodulating each electrical signal by responding to signals at a modulation frequency of the corresponding polarization-modulated light beam and ignoring noise affecting signals outside the modulation frequency; and analyzing the demodulated electrical signal to identify the resonant condition which indicates whether the biological substance is located in the sensing region of the respective grating-coupled waveguide sensor.

15. The method of claim 14, wherein said biological substance is a cell, molecule, protein, drug, chemical compound, nucleic acid, peptide or carbohydrate.

16. The method of claim 14, wherein phase information within each demodulated electrical signal is used to identify the resonant condition which indicates whether the biological substance is located in the sensing region of the respective grating-coupled waveguide sensor.

17. The method of claim 14, wherein amplitude information within each demodulated electrical signal is used to identify the resonant condition which indicates whether the biological substance is located in the sensing region of the respective grating-coupled waveguide sensor.

18. The method of claim 14, wherein said processing step utilizes an angular scanning approach to scan the polarization-modulated light beam to enable the detection of a resonant angle which indicates whether the biological substance is located in the sensing region of the respective grating-coupled waveguide sensor.

19. The method of claim 14, wherein said processing step utilizes an angular scanning approach to scan the amplitude modulated light beam to enable the detection of a resonant angle which indicates whether the biological substance is located in the sensing region of the respective grating-coupled waveguide sensor.

20. The method of claim 14, wherein said processing step utilizes a wavelength scanning approach to scan the polarization-modulated light beam to enable the detection of a resonant wavelength which indicates whether the biological substance is located in the sensing region of the respective grating-coupled waveguide sensor.

21. The method of claim 14, wherein said processing step utilizes a wavelength scanning approach to scan the amplitude modulated light beam to enable the detection of a resonant wavelength which indicates whether the biological substance is located in the sensing region of the respective grating-coupled waveguide sensor.

22. The method of claim 14, wherein said one or more grating-coupled waveguide sensors are located within a microplate.

* * * * *